(12) United States Patent
Malcolm

(10) Patent No.: US 10,993,928 B2
(45) Date of Patent: May 4, 2021

(54) COMPOSITIONS COMPRISING NON-CRYSTALLINE FORMS OF CANNABIDIOL

(71) Applicant: Natural Extraction Systems, LLC, Boulder, CO (US)

(72) Inventor: Nixon Malcolm, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 16 days.

(21) Appl. No.: 16/408,428

(22) Filed: May 9, 2019

(65) Prior Publication Data

US 2020/0338038 A1 Oct. 29, 2020

Related U.S. Application Data

(60) Provisional application No. 62/839,564, filed on Apr. 26, 2019, provisional application No. 62/845,231, filed on May 8, 2019.

(51) Int. Cl.
| | | |
|---|---|---|
| *A61K 31/352* | (2006.01) | |
| *A24F 47/00* | (2020.01) | |
| *B01D 11/02* | (2006.01) | |
| *A61K 36/185* | (2006.01) | |

(52) U.S. Cl.
CPC .......... *A61K 31/352* (2013.01); *A24F 47/002* (2013.01); *A61K 36/185* (2013.01); *B01D 11/0203* (2013.01)

(58) Field of Classification Search
None
See application file for complete search history.

(56) References Cited

U.S. PATENT DOCUMENTS

| | | | |
|---|---|---|---|
| 9,730,911 B2 | 8/2017 | Verzura et al. | |
| 2015/0105455 A1* | 4/2015 | Bjorncrantz | A61K 9/007 514/454 |
| 2016/0279073 A1* | 9/2016 | Donsky | A23L 2/52 |
| 2016/0309774 A1* | 10/2016 | Wand | A61K 47/06 |
| 2017/0021025 A1* | 1/2017 | Naheed | A61K 36/185 |
| 2017/0295845 A1 | 10/2017 | Bajpai et al. | |
| 2018/0221396 A1* | 8/2018 | Chadeayne | A61K 31/4045 |
| 2019/0030101 A1* | 1/2019 | Cooper | A61K 31/353 |
| 2019/0183853 A1* | 6/2019 | Levy | A61K 47/22 |
| 2019/0231833 A1* | 8/2019 | Garti | A61K 9/7023 |
| 2019/0254988 A1* | 8/2019 | Archibald | A61K 31/05 |
| 2019/0298683 A1* | 10/2019 | Friedman | A61K 31/045 |

* cited by examiner

*Primary Examiner* — Michael J Felton
*Assistant Examiner* — Taryn Trace Willett
(74) *Attorney, Agent, or Firm* — Foley Hoag LLP; David P. Halstead; Laura A. Wzorek

(57) ABSTRACT

Various aspects of this patent document relate to liquid compositions comprising cannabidiol, which have either freezing points or glass-liquid transition temperatures less than the melting point of pure cannabidiol.

17 Claims, No Drawings

COMPOSITIONS COMPRISING NON-CRYSTALLINE FORMS OF CANNABIDIOL

CROSS-REFERENCE TO RELATED APPLICATIONS

This patent application claims priority to U.S. Provisional Patent Application No. 62/839,564, filed Apr. 26, 2019, and U.S. Provisional Patent Application No. 62/845,231, filed May 8, 2019, each of which is incorporated by reference in its entirety.

BACKGROUND

Cannabidiol exists in a crystalline form at room temperature, which has a melting point of 151 degrees Fahrenheit (66 degrees Celsius). Crystalline cannabidiol lacks robust bioavailability, for example, because the human body is incapable of melting it. The pharmaceutical EPIDIOLEX® contains cannabidiol dissolved in sesame seed oil to increase bioavailability.

Consumers also vaporize and inhale cannabidiol to increase bioavailability. Cannabidiol crystallization confounds vaporization in electronic cigarettes and vaporizers because crystallization inhibits the flow of cannabidiol toward a heating element. Prior art methods to inhibit the crystallization of cannabidiol for use in electronic cigarettes and vaporizers include the dissolution of cannabidiol in organic solvents such as propylene glycol, glycerol, and triglycerides. Organic solvents dilute the cannabidiol, however, and present unknown health risks. Improved cannabidiol formulations are therefore desirable.

SUMMARY

Various aspects of this patent document relate to liquid compositions comprising cannabidiol, which have freezing points or glass-liquid transition temperatures less than the melting point of pure cannabidiol.

DETAILED DESCRIPTION

This patent document discloses that the melting point of cannabidiol can be lowered by dissolving a small amount of an organic solute in liquid cannabidiol. The melting point of cannabidiol can be reduced to less than 70 degrees Fahrenheit (or less than 21 degrees Celsius), for example, to provide concentrated cannabidiol compositions that are liquids at room temperature. This discovery allows novel products including concentrated cannabidiol vape oil.

Various aspects of this patent document relate to a composition comprising cannabidiol. The term "cannabidiol" refers to 2-[(1R,6R)-6-isopropenyl-3-methylcyclohex-2-en-1-yl]-5-pentylbenzene-1,3-diol.

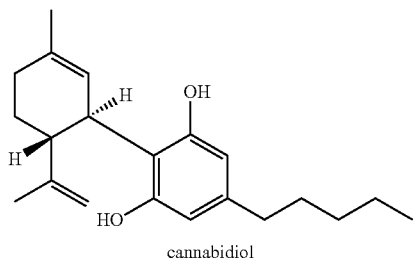 [SMILES: C=C(C)[C@@H]1CCC(C)=C[C@H]1c1c(O)cc(CCCCC)cc1O]

cannabidiol

In some embodiments, a composition comprises cannabidiol at a concentration of 50% to 99.5% by mass and one or more solutes selected from terpenes, terpene alcohols, and terpenoids at a combined concentration of 0.5% to 40% by mass, in which the one or more solutes are dissolved in the cannabidiol; the composition has either a freezing point or a glass-liquid transition temperature; and the freezing point or the glass-liquid transition temperature is either at least 50 degrees Fahrenheit less than the freezing point of pure cannabidiol or at least 27 degrees Celsius less than the freezing point of pure cannabidiol.

In some embodiments, a composition comprises cannabidiol at a concentration of 65% to 99.5% by mass and one or more solutes selected from terpenes, terpene alcohols, and terpenoids at a combined concentration of 0.5% to 35% by mass, in which the one or more solutes are dissolved in the cannabidiol; the composition has either a freezing point or a glass-liquid transition temperature; and the freezing point or the glass-liquid transition temperature is either at least 50 degrees Fahrenheit less than the freezing point of pure cannabidiol or at least 27 degrees Celsius less than the freezing point of pure cannabidiol.

In some embodiments, a composition comprises cannabidiol at a concentration of 70% to 99.5% by mass and one or more solutes selected from terpenes, terpene alcohols, and terpenoids at a combined concentration of 0.5% to 30% by mass, in which the one or more solutes are dissolved in the cannabidiol; the composition has either a freezing point or a glass-liquid transition temperature; and the freezing point or the glass-liquid transition temperature is either at least 50 degrees Fahrenheit less than the freezing point of pure cannabidiol or at least 27 degrees Celsius less than the freezing point of pure cannabidiol.

In some embodiments, a composition has a freezing point; the composition lacks a glass-liquid transition temperature; and the freezing point is less than either 70 degrees Fahrenheit or 21 degrees Celsius. In some specific embodiments, a composition has a freezing point; the composition lacks a glass-liquid transition temperature; and the freezing point is less than either 60 degrees Fahrenheit or 15 degrees Celsius.

In some embodiments, a composition has a glass-liquid transition temperature; the composition lacks a freezing point; and the glass-liquid transition temperature is less than either 70 degrees Fahrenheit or 21 degrees Celsius. In some specific embodiments, a composition has a glass-liquid transition temperature; the composition lacks a freezing point; and the glass-liquid transition temperature is less than either 60 degrees Fahrenheit or 15 degrees Celsius.

In some embodiments, a composition lacks crystals of cannabidiol at a concentration greater than 5% by mass. In some specific embodiments, a composition is essentially free of crystals of cannabidiol. In some very specific embodiments, a composition lacks crystals of cannabidiol.

In some embodiments, a composition comprises cannabidiol at a concentration of 70% to 99% by mass. In some specific embodiments, a composition comprises cannabidiol at a concentration of 75% to 95% by mass. In some very specific embodiments, a composition comprises cannabidiol at a concentration of 80% to 90% by mass.

In some embodiments, a composition lacks tetrahydrocannabinol at a concentration greater than 0.3% by mass. In some specific embodiments, a composition is essentially free of tetrahydrocannabinol. In some very specific embodiments, a composition lacks tetrahydrocannabinol.

In some embodiments, a composition comprises tetrahydrocannabinol at a concentration greater than 0.3% by mass; the composition comprises cannabidiol and tetrahydrocannabinol at a ratio of 3:1 to 200:1 by mass; and the tetrahydrocannabinol is dissolved in the cannabidiol. In some specific embodiments, a composition comprises tetrahydrocannabinol at a concentration greater than 0.3% by mass; the composition comprises cannabidiol and tetrahydrocannabinol at a ratio of 4:1 to 150:1 by mass; and the tetrahydrocannabinol is dissolved in the cannabidiol. In some very specific embodiments, a composition comprises tetrahydrocannabinol at a concentration greater than 0.3% by mass; the composition comprises cannabidiol and tetrahydrocannabinol at a ratio of 5:1 to 100:1 by mass; and the tetrahydrocannabinol is dissolved in the cannabidiol.

In some embodiments, a composition comprises (6aS,10aR)-6,6,9-trimethyl-3-pentyl-6a,7,8,10a-tetrahydro-6H-benzo[c]chromen-1-ol at a concentration of 0.05% to 5% by mass, in which the (6aS,10aR)-6,6,9-trimethyl-3-pentyl-6a,7,8,10a-tetrahydro-6H-benzo[c]chromen-1-ol is dissolved in cannabidiol of the composition.

In some embodiments, a composition comprises molecules having a boiling point lower than either 360 degrees Fahrenheit or 182 degrees Celsius at a combined concentration of at least 90% by mass. In some specific embodiments, a composition comprises molecules having a boiling point lower than either 360 degrees Fahrenheit or 182 degrees Celsius at a combined concentration of at least 95% by mass. In some very specific embodiments, a composition comprises molecules having a boiling point lower than either 360 degrees Fahrenheit or 182 degrees Celsius at a combined concentration of at least 98% by mass.

The term "boiling point" refers to the boiling point of a purified molecule at atmospheric pressure.

In some embodiments, a composition lacks propylene glycol, glycerol, triglycerides, phospholipids, fatty acids, and waxes at a combined concentration greater than 10% by mass. In some specific embodiments, a composition lacks propylene glycol, glycerol, triglycerides, phospholipids, fatty acids, and waxes at a combined concentration greater than 5% by mass. In some very specific embodiments, a composition is essentially free of propylene glycol, glycerol, triglycerides, phospholipids, fatty acids, and waxes.

In some embodiments, a composition is a liquid.

In some embodiments, a composition has a viscosity, and the viscosity is less than 100 pascal-seconds at a temperature of either 70 degrees Fahrenheit or 21 degrees Celsius. In some specific embodiments, a composition has a viscosity, and the viscosity is 50 millipascal-seconds to 50 pascal-seconds at a temperature of either 70 degrees Fahrenheit or 21 degrees Celsius. In some very specific embodiments, a composition has a viscosity, and the viscosity is 0.1 pascal-seconds to 25 pascal-seconds at a temperature of either 70 degrees Fahrenheit or 21 degrees Celsius.

In some embodiments, a composition comprises one or more solutes, and the one or more solutes comprise one or more of alpha-bisabolol, alpha-phellandrene, alpha-pinene, alpha-terpinene, alpha-terpineol, beta-caryophyllene, beta-pinene, borneol, cadinene, camphene, camphor, caryophyllene oxide, citral, citronellol, delta-3-carene, eucalyptol, eugenol, gamma-terpinene, geraniol, guaiol, humulene, isopulegol, limonene, linalool, myrcene, nerol, nerolidol, ocimene, para-cymene, phytol, pulegone, terpineol, terpinolene, and valencene at a combined concentration of 0.5% to 40% by mass. In some specific embodiments, a composition comprises one or more solutes, and the one or more solutes comprise one or more of alpha-bisabolol, alpha-phellandrene, alpha-pinene, alpha-terpinene, alpha-terpineol, beta-caryophyllene, beta-pinene, borneol, cadinene, camphene, camphor, caryophyllene oxide, citral, citronellol, delta-3-carene, eucalyptol, eugenol, gamma-terpinene, geraniol, guaiol, humulene, isopulegol, limonene, linalool, myrcene, nerol, nerolidol, ocimene, para-cymene, phytol, pulegone, terpineol, terpinolene, and valencene at a combined concentration of 1% to 35% by mass.

In some embodiments, a composition comprises one or more solutes, and the one or more solutes comprise one or more of alpha-bisabolol, beta-caryophyllene, guaiol, humulene, limonene, myrcene, and terpinolene at a combined concentration of 0.5% to 40% by mass. In some specific embodiments, a composition comprises one or more solutes, and the one or more solutes comprise one or more of alpha-bisabolol, beta-caryophyllene, guaiol, humulene, limonene, myrcene, and terpinolene at a combined concentration of 1% to 35% by mass.

In some embodiments, a composition comprises cannabidiol at a concentration of 65% to 99.5% by mass and one or more solutes, in which the composition lacks crystals of cannabidiol; the one or more solutes are dissolved in the cannabidiol; the one or more solutes comprise one or more of alpha-bisabolol, beta-caryophyllene, guaiol, humulene, limonene, myrcene, and terpinolene, which are present in the composition at a combined concentration of 0.5% to 35% by mass; the composition comprises molecules having a boiling point lower than either 360 degrees Fahrenheit or 182 degrees Celsius at a combined concentration of at least 95% by mass; the composition lacks tetrahydrocannabinol at a concentration greater than 0.3% by mass; the composition lacks propylene glycol, glycerol, triglycerides, phospholipids, fatty acids, and waxes at a combined concentration greater than 5% by mass; the composition has a glass-liquid transition temperature; the glass-liquid transition temperature is less than either 70 degrees Fahrenheit or 21 degrees Celsius; the composition is a liquid; the composition lacks a freezing point; the composition has a viscosity; and the viscosity is 50 millipascal-seconds to 50 pascal-seconds at a temperature of either 70 degrees Fahrenheit or 21 degrees Celsius.

In some embodiments, a composition comprises cannabidiol at a concentration of 65% to 99.5% by mass and one or more solutes, in which the composition lacks crystals of cannabidiol; the one or more solutes are dissolved in the cannabidiol; the one or more solutes comprise one or more of alpha-bisabolol, beta-caryophyllene, guaiol, humulene, limonene, myrcene, and terpinolene, which are present in the composition at a combined concentration of 0.5% to 35% by mass; the composition comprises molecules having a boiling point lower than either 360 degrees Fahrenheit or 182 degrees Celsius at a combined concentration of at least 95% by mass; the composition comprises tetrahydrocannabinol at a concentration greater than 0.3% by mass; the tetrahydrocannabinol is dissolved in the cannabidiol; the composition comprises cannabidiol and tetrahydrocannabinol at a ratio of 3:1 to 200:1 by mass; the composition lacks propylene glycol, glycerol, triglycerides, phospholipids, fatty acids, and waxes at a combined concentration greater than 5% by mass; the composition has a glass-liquid transition temperature; the glass-liquid transition temperature is less than either 70 degrees Fahrenheit or 21 degrees Celsius; the composition is a liquid; the composition lacks a freezing point; the composition has a viscosity; and the viscosity is 50 millipascal-seconds to 50 pascal-seconds at a temperature of either 70 degrees Fahrenheit or 21 degrees Celsius.

Various aspects of this patent document relate to a container comprising a heating element and a chamber that contains a composition described in this patent document, in which the heating element is in thermal communication with the composition.

Various aspects of this patent document relate to a method to manufacture a composition described in this patent document.

In some embodiments, a method comprises providing a cannabinoid composition comprising cannabidiol at a concentration of 75% to 99.9% by mass; heating the cannabinoid composition to provide liquid-phase cannabidiol; providing a solute composition comprising one or more terpenes, terpene alcohols, and terpenoids at a combined concentration of 50% to 99.9% by mass; mixing the cannabinoid composition with the solute composition to dissolve the one or more terpenes, terpene alcohols, and terpenoids in the liquid-phase cannabidiol; and producing a liquid cannabidiol composition, which is a composition according to the description set forth above. In some specific embodiments, a method comprises providing a cannabinoid composition comprising cannabidiol at a concentration of 75% to 99.9% by mass; heating the cannabinoid composition to provide liquid-phase cannabidiol; providing a solute composition comprising one or more terpenes, terpene alcohols, and terpenoids at a combined concentration of 50% to 99.9% by mass; mixing the cannabinoid composition with the solute composition to dissolve the one or more terpenes, terpene alcohols, and terpenoids in the liquid-phase cannabidiol; and producing a liquid cannabidiol composition comprising the one or more terpenes, terpene alcohols, and terpenoids dissolved in the liquid-phase cannabidiol, in which the liquid cannabidiol composition is a liquid; the liquid cannabidiol composition comprises cannabidiol at a concentration of 50% to 99.5% by mass; the liquid cannabidiol composition lacks crystals of cannabidiol; the liquid cannabidiol composition has either a freezing point or a glass-liquid transition temperature; and the freezing point or the glass-liquid transition temperature is either less than 70 degrees Fahrenheit or less than 21 degrees Celsius.

In some embodiments, a cannabinoid composition is a solid at either 70 degrees Fahrenheit or 21 degrees Celsius; the cannabinoid composition is a super-cooled liquid at either 70 degrees Fahrenheit or 21 degrees Celsius; or the cannabinoid composition is a liquid comprising crystals of cannabidiol at either 70 degrees Fahrenheit or 21 degrees Celsius.

In some embodiments, a cannabinoid composition comprises crystals of cannabidiol, and heating the cannabinoid composition melts the crystals of cannabidiol.

In some embodiments, a liquid cannabidiol composition has a freezing point and lacks a glass-liquid transition temperature; and the freezing point is less than either 70 degrees Fahrenheit or 21 degrees Celsius. In some specific embodiments, a liquid cannabidiol composition has a freezing point and lacks a glass-liquid transition temperature; and the freezing point is less than either 60 degrees Fahrenheit or 15 degrees Celsius.

In some embodiments, a liquid cannabidiol composition has a glass-liquid transition temperature and lacks a freezing point; and the glass-liquid transition temperature is less than either 70 degrees Fahrenheit or 21 degrees Celsius. In some specific embodiments, a liquid cannabidiol composition has a glass-liquid transition temperature and lacks a freezing point; and the glass-liquid transition temperature is less than either 60 degrees Fahrenheit or 15 degrees Celsius. In some specific embodiments, a cannabinoid composition has a freezing point and lacks a glass-liquid transition temperature; a liquid cannabidiol composition has a glass-liquid transition temperature and lacks a freezing point; and the glass-liquid transition temperature of the liquid cannabidiol composition is less than either 70 degrees Fahrenheit or 21 degrees Celsius.

In some embodiments, a cannabinoid composition lacks tetrahydrocannabinol at a concentration greater than 0.3% by mass. In some specific embodiments, a cannabinoid composition is essentially free of tetrahydrocannabinol. In some very specific embodiments, a cannabinoid composition lacks tetrahydrocannabinol.

In some embodiments, producing a liquid cannabidiol composition comprises producing a liquid cannabidiol composition comprising cannabidiol and tetrahydrocannabinol at a ratio of 3:1 to 200:1 by mass, in which the tetrahydrocannabinol is dissolved in the cannabidiol. In some specific embodiments, producing a liquid cannabidiol composition comprises producing a liquid cannabidiol composition comprising cannabidiol and tetrahydrocannabinol at a ratio of 4:1 to 150:1 by mass, in which the tetrahydrocannabinol is dissolved in the cannabidiol. In some very specific embodiments, producing a liquid cannabidiol composition comprises producing a liquid cannabidiol composition comprising cannabidiol and tetrahydrocannabinol at a ratio of 5:1 to 100:1 by mass, in which the tetrahydrocannabinol is dissolved in the cannabidiol.

In some embodiments, a cannabinoid composition comprises (6aS,10aR)-6,6,9-trimethyl-3-pentyl-6a,7,8,10a-tetrahydro-6H-benzo[c]chromen-1-ol at a concentration of 0.05% to 5% by mass; and producing a liquid cannabidiol composition comprises producing a liquid cannabidiol composition comprising (6aS,10aR)-6,6,9-trimethyl-3-pentyl-6a,7,8,10a-tetrahydro-6H-benzo[c]chromen-1-ol at a concentration of 0.05% to 5% by mass.

In some embodiments, a cannabinoid composition comprises molecules having a boiling point lower than either 360 degrees Fahrenheit or 182 degrees Celsius at a combined concentration of at least 95% by mass; and producing a liquid cannabidiol composition comprises producing a liquid cannabidiol composition comprising molecules having a boiling point lower than either 360 degrees Fahrenheit or 182 degrees Celsius at a combined concentration of at least 95% by mass.

In some embodiments, producing a liquid cannabidiol composition comprises producing a liquid cannabidiol composition that lacks propylene glycol, glycerol, triglycerides, phospholipids, fatty acids, and waxes at a combined concentration greater than 5% by mass. In some specific embodiments, producing a liquid cannabidiol composition comprises producing a liquid cannabidiol composition that is essentially free of propylene glycol, glycerol, triglycerides, phospholipids, fatty acids, and waxes. In some very specific embodiments, producing a liquid cannabidiol composition comprises producing a liquid cannabidiol composition that lacks propylene glycol, glycerol, triglycerides, phospholipids, fatty acids, and waxes.

In some embodiments, producing a liquid cannabidiol composition comprises producing a liquid cannabidiol composition that has a viscosity of less than 100 pascal-seconds at a temperature of either 70 degrees Fahrenheit or 21 degrees Celsius. In some specific embodiments, producing a liquid cannabidiol composition comprises producing a liquid cannabidiol composition that has a viscosity of 50 millipascal-seconds to 50 pascal-seconds at a temperature of either 70 degrees Fahrenheit or 21 degrees Celsius. In some specific embodiments, producing a liquid cannabidiol composition comprises producing a liquid cannabidiol composition that has a viscosity of 0.1 pascal-seconds to 25 pascal-seconds at a temperature of either 70 degrees Fahrenheit or 21 degrees Celsius.

In some embodiments, a cannabinoid composition has a viscosity greater than 25 pascal-seconds at a temperature of either 70 degrees Fahrenheit or 21 degrees Celsius; and producing a liquid cannabidiol composition comprises producing a liquid cannabidiol composition having a viscosity of less than 25 pascal-seconds at a temperature of either 70 degrees Fahrenheit or 21 degrees Celsius.

In some embodiments, a solute composition comprises one or more of alpha-bisabolol, alpha-phellandrene, alpha-pinene, alpha-terpinene, alpha-terpineol, beta-caryophyllene, beta-pinene, borneol, cadinene, camphene, camphor, caryophyllene oxide, citral, citronellol, delta-3-carene, eucalyptol, eugenol, gamma-terpinene, geraniol, guaiol, humulene, isopulegol, limonene, linalool, myrcene, nerol, nerolidol, ocimene, para-cymene, phytol, pulegone, terpineol, terpinolene, and valencene at a combined concentration greater than 50% by mass; and producing a liquid cannabidiol composition comprises producing a liquid cannabidiol composition comprising one or more of alpha-bisabolol, alpha-phellandrene, alpha-pinene, alpha-terpinene, alpha-terpineol, beta-caryophyllene, beta-pinene, borneol, cadinene, camphene, camphor, caryophyllene oxide, citral, citronellol, delta-3-carene, eucalyptol, eugenol, gamma-terpinene, geraniol, guaiol, humulene, isopulegol, limonene, linalool, myrcene, nerol, nerolidol, ocimene, para-cymene, phytol, pulegone, terpineol, terpinolene, and valencene at a combined concentration of 0.5% to 40% by mass. In some specific embodiments, a solute composition comprises one or more of alpha-bisabolol, alpha-phellandrene, alpha-pinene, alpha-terpinene, alpha-terpineol, beta-caryophyllene, beta-pinene, borneol, cadinene, camphene, camphor, caryophyllene oxide, citral, citronellol, delta-3-carene, eucalyptol, eugenol, gamma-terpinene, geraniol, guaiol, humulene, isopulegol, limonene, linalool, myrcene, nerol, nerolidol, ocimene, para-cymene, phytol, pulegone, terpineol, terpinolene, and valencene at a combined concentration greater than 90% by mass; and producing a liquid cannabidiol composition comprises producing a liquid cannabidiol composition comprising one or more of alpha-bisabolol, alpha-phellandrene, alpha-pinene, alpha-terpinene, alpha-terpineol, beta-caryophyllene, beta-pinene, borneol, cadinene, camphene, camphor, caryophyllene oxide, citral, citronellol, delta-3-carene, eucalyptol, eugenol, gamma-terpinene, geraniol, guaiol, humulene, isopulegol, limonene, linalool, myrcene, nerol, nerolidol, ocimene, para-cymene, phytol, pulegone, terpineol, terpinolene, and valencene at a combined concentration of 1% to 35% by mass.

In some embodiments, a solute composition comprises one or more of alpha-bisabolol, beta-caryophyllene, guaiol, humulene, limonene, myrcene, and terpinolene at a combined concentration greater than 50% by mass; and producing a liquid cannabidiol composition comprises producing a liquid cannabidiol composition comprising one or more of alpha-bisabolol, beta-caryophyllene, guaiol, humulene, limonene, myrcene, and terpinolene at a combined concentration of 0.5% to 40% by mass. In some specific embodiments, a solute composition comprises one or more of alpha-bisabolol, beta-caryophyllene, guaiol, humulene, limonene, myrcene, and terpinolene at a combined concentration greater than 90% by mass; and producing a liquid cannabidiol composition comprises producing a liquid cannabidiol composition comprising one or more of alpha-bisabolol, beta-caryophyllene, guaiol, humulene, limonene, myrcene, and terpinolene at a combined concentration of 1% to 35% by mass.

In some embodiments, a method comprises providing a cannabinoid composition comprising cannabidiol at a concentration of 75% to 99.9% by mass; heating the cannabinoid composition to provide liquid-phase cannabidiol; providing a solute composition comprising one or more terpenes, terpene alcohols, and terpenoids at a combined concentration of 50% to 99.9% by mass; mixing the cannabinoid composition with the solute composition to dissolve the one or more terpenes, terpene alcohols, and terpenoids in the liquid-phase cannabidiol; and producing a liquid cannabidiol composition comprising the one or more terpenes, terpene alcohols, and terpenoids dissolved in the liquid-phase cannabidiol such that the liquid cannabidiol composition has a viscosity of less than 100 pascal-seconds at a temperature of either 70 degrees Fahrenheit or 21 degrees Celsius, in which: the cannabinoid composition has a freezing point; the cannabinoid composition lacks a glass-liquid transition temperature; the cannabinoid composition is either a solid, a super-cooled liquid, or a liquid comprising crystals of cannabidiol at either 70 degrees Fahrenheit or 21 degrees Celsius; the cannabinoid composition comprises molecules having a boiling point lower than either 360 degrees Fahrenheit or 182 degrees Celsius at a combined concentration of at least 95% by mass; producing the liquid cannabidiol composition comprises producing a liquid cannabidiol composition comprising molecules having a boiling point lower than either 360 degrees Fahrenheit or 182 degrees Celsius at a combined concentration of at least 95% by mass; the liquid cannabidiol composition is a liquid; producing the liquid cannabidiol composition comprises producing a liquid cannabidiol composition that lacks propylene glycol, glycerol, triglycerides, phospholipids, fatty acids, and waxes at a combined concentration greater than 5% by mass; the liquid cannabidiol composition comprises cannabidiol at a concentration of 50% to 99.5% by mass; the liquid cannabidiol composition lacks crystals of cannabidiol; the liquid cannabidiol composition has either a freezing point or a glass-liquid transition temperature; and the freezing point or the glass-liquid transition temperature of the liquid cannabidiol composition is either less than 70 degrees Fahrenheit or less than 21 degrees Celsius.

In some embodiments, a method comprises providing a cannabinoid composition comprising cannabidiol at a concentration of 75% to 99.9% by mass; heating the cannabinoid composition to provide liquid-phase cannabidiol; providing a solute composition comprising one or more terpenes, terpene alcohols, and terpenoids at a combined concentration of 50% to 99.9% by mass; mixing the cannabinoid composition with the solute composition to dissolve the one or more terpenes, terpene alcohols, and terpenoids in the liquid-phase cannabidiol; and producing a liquid cannabidiol composition comprising the one or more terpenes, terpene alcohols, and terpenoids dissolved in the liquid-phase cannabidiol such that the liquid cannabidiol composition has a viscosity of less than 100 pascal-seconds at a temperature of either 70 degrees Fahrenheit or 21 degrees Celsius, in which: the cannabinoid composition has a freezing point; the cannabinoid composition lacks a glass-liquid transition temperature; the cannabinoid composition is either a solid, a super-cooled liquid, or a liquid comprising crystals of cannabidiol at either 70 degrees Fahrenheit or 21 degrees Celsius; the cannabinoid composition comprises molecules having a boiling point lower than either 360 degrees Fahrenheit or 182 degrees Celsius at a combined concentration of at least 95% by mass; producing the liquid cannabidiol composition comprises producing a liquid cannabidiol composition comprising molecules having a boiling point lower than either 360 degrees Fahrenheit or 182 degrees Celsius at a combined concentration of at least 95% by mass; the liquid cannabidiol composition is a liquid; producing the liquid cannabidiol composition comprises producing a liquid cannabidiol composition that lacks propylene glycol, glycerol, triglycerides, phospholipids, fatty acids, and waxes at a combined concentration greater than 5% by mass; the liquid cannabidiol composition comprises cannabidiol at a concentration of 50% to 99.5% by mass; the liquid cannabidiol composition lacks crystals of cannabidiol; producing the liquid cannabidiol composition comprises producing a liquid cannabidiol composition that has a glass-liquid transition temperature and that lacks a freezing point; and the glass-liquid transition temperature of the liquid cannabidiol composition is either less than 70 degrees Fahrenheit or less than 21 degrees Celsius.

Various aspects of this patent document relate to a method to administer cannabidiol comprising providing a composition described in this patent document; heating the composition to provide at least 1 milligram of cannabidiol vapor; and inhaling the cannabidiol vapor.

In some embodiments, a method comprises providing a composition comprising cannabidiol at a concentration of 65% to 99.5% by mass and one or more solutes selected from terpenes, terpene alcohols, and terpenoids at a concentration of 0.5% to 35% by mass; heating the composition to provide at least 1 milligram of cannabidiol vapor; and inhaling the cannabidiol vapor, in which: the composition is a liquid; the one or more solutes are dissolved in the cannabidiol; and the composition has either a freezing point or a gas-liquid transition temperature of less than either 70 degrees Fahrenheit or 21 degrees Celsius.

In some embodiments, heating a composition comprises conductively heating at least a portion of the composition to a temperature of at least 330 degrees Fahrenheit or 165 degrees Celsius. In some specific embodiments, heating a composition comprises conductively heating at least a portion of the composition to a temperature of 330 to 440 degrees Fahrenheit or 165 to 227 degrees Celsius.

In some embodiments, providing a composition comprises providing a container containing the composition, in which the container is configured to position the composition in thermal communication with a heating element; and conductively heating at least a portion of the composition comprises transferring heat from the heating element to the portion of the composition.

In some embodiments, a method comprises positioning a composition in thermal communication with a heating element.

In some embodiments, a container comprises a chamber; the container contains a composition within the chamber; the chamber has a volume; the composition has a volume; the volume of the chamber is greater than the volume of the composition; the chamber comprises a surface that insulates heat and a surface that conducts heat; and positioning the composition in thermal communication with a heating element comprises directing the composition from the surface that insulates heat to the surface that conducts heat.

In some embodiments, a container comprises a chamber; the container contains a composition within the chamber; the chamber comprises a surface that conducts heat; the surface that conducts heat has a surface area; the composition is in thermal communication with a heating element when both the surface that conducts heat is in thermal communication with the heating element and the composition is in physical contact with a percentage of the surface area of the surface that conducts heat; the percentage of the surface area of the surface that conducts heat that is in physical contact with the composition correlates with a rate at which heating the composition provides cannabidiol vapor; heating the composition to provide at least 1 milligram of cannabidiol vapor decreases the percentage of the surface area of the surface that conducts heat that is in physical contact with the composition; and a method comprises directing the composition to the surface that conducts heat to increase the percentage of the surface area of the surface that conducts heat that is in physical contact with the composition.

In some embodiments, a composition of a method has a viscosity of less than 100 pascal-seconds at a temperature of either 70 degrees Fahrenheit or 21 degrees Celsius. In some specific embodiments, a composition has a viscosity of 50 millipascal-seconds to 50 pascal-seconds at a temperature of either 70 degrees Fahrenheit or 21 degrees Celsius. In some very specific embodiments, a composition has a viscosity of 0.1 pascal-seconds to 25 pascal-seconds at a temperature of either 70 degrees Fahrenheit or 21 degrees Celsius.

In some embodiments, a composition of a method has a gas-liquid transition temperature, the composition lacks a freezing point, and the gas-liquid transition temperature is less than either 70 degrees Fahrenheit or 21 degrees Celsius. In some specific embodiments, a composition has a gas-liquid transition temperature, the composition lacks a freezing point, and the gas-liquid transition temperature is less than either 60 degrees Fahrenheit or 15 degrees Celsius.

In some embodiments, a composition of a method has a freezing point, the composition lacks a gas-liquid transition temperature, and the freezing point is less than either 70 degrees Fahrenheit or 21 degrees Celsius. In some embodiments, a composition has a freezing point, the composition lacks a gas-liquid transition temperature, and the freezing point is less than either 60 degrees Fahrenheit or 15 degrees Celsius.

In some embodiments, a composition of a method lacks propylene glycol, glycerol, triglycerides, phospholipids, fatty acids, and waxes at a combined concentration greater than 5% by mass. In some specific embodiments, a composition is essentially free of propylene glycol, glycerol, triglycerides, phospholipids, fatty acids, and waxes. In some very specific embodiments, a composition lacks propylene glycol, glycerol, triglycerides, phospholipids, fatty acids, and waxes.

In some embodiments, a composition of a method comprises molecules having a boiling point lower than either 360 degrees Fahrenheit or 182 degrees Celsius at a combined concentration of at least 90% by mass. In some specific embodiments, a composition comprises molecules having a boiling point lower than either 360 degrees Fahrenheit or 182 degrees Celsius at a combined concentration of at least 95% by mass. In some very specific embodiments, a composition comprises molecules having a boiling point lower than either 360 degrees Fahrenheit or 182 degrees Celsius at a combined concentration of at least 98% by mass.

In some embodiments, a composition of a method lacks tetrahydrocannabinol at a concentration greater than 0.3% by mass. In some specific embodiments, a composition is essentially free of tetrahydrocannabinol. In some very specific embodiments, a composition lacks tetrahydrocannabinol.

In some embodiments, a composition of a method comprises cannabidiol and tetrahydrocannabinol at a ratio of 3:1 to 200:1 by mass, in which the tetrahydrocannabinol is dissolved in the cannabidiol. In some specific embodiments, a composition comprises cannabidiol and tetrahydrocannabinol at a ratio of 4:1 to 150:1 by mass, in which the tetrahydrocannabinol is dissolved in the cannabidiol. In some very specific embodiments, a composition comprises cannabidiol and tetrahydrocannabinol at a ratio of 5:1 to 100:1 by mass, in which the tetrahydrocannabinol is dissolved in the cannabidiol.

In some embodiments, a composition of a method comprises (6aS,10aR)-6,6,9-trimethyl-3-pentyl-6a,7,8,10a-tetrahydro-6H-benzo[c]chromen-1-ol at a concentration of 0.05% to 5% by mass, in which the (6aS,10aR)-6,6,9-trimethyl-3-pentyl-6a,7,8,10a-tetrahydro-6H-benzo[c]chromen-1-ol is dissolved in cannabidiol of the composition.

In some embodiments, a composition of a method comprises one or more solutes comprising one or more of alpha-bisabolol, alpha-phellandrene, alpha-pinene, alpha-terpinene, alpha-terpineol, beta-caryophyllene, beta-pinene, borneol, cadinene, camphene, camphor, caryophyllene oxide, citral, citronellol, delta-3-carene, eucalyptol, eugenol, gamma-terpinene, geraniol, guaiol, humulene, isopulegol, limonene, linalool, myrcene, nerol, nerolidol, ocimene, para-cymene, phytol, pulegone, terpineol, terpinolene, and valencene at a combined concentration of 0.5% to 40% by mass. In some specific embodiments, a composition of a method comprises one or more solutes comprising one or more of alpha-bisabolol, alpha-phellandrene, alpha-pinene, alpha-terpinene, alpha-terpineol, beta-caryophyllene, beta-pinene, borneol, cadinene, camphene, camphor, caryophyllene oxide, citral, citronellol, delta-3-carene, eucalyptol, eugenol, gamma-terpinene, geraniol, guaiol, humulene, isopulegol, limonene, linalool, myrcene, nerol, nerolidol, ocimene, para-cymene, phytol, pulegone, terpineol, terpinolene, and valencene at a combined concentration of 1% to 35% by mass.

In some embodiments, a composition of a method comprises one or more solutes, and the one or more solutes comprise one or more of alpha-bisabolol, beta-caryophyllene, guaiol, humulene, limonene, myrcene, and terpinolene at a combined concentration of 0.5% to 40% by mass. In some specific embodiments, a composition comprises one or more solutes, and the one or more solutes comprise one or more of alpha-bisabolol, beta-caryophyllene, guaiol, humulene, limonene, myrcene, and terpinolene at a combined concentration of 1% to 35% by mass.

In some embodiments, a method to administer cannabidiol comprises providing a container containing a composition comprising cannabidiol at a concentration of 60% to 99.5% by mass and one or more solutes selected from terpenes, terpene alcohols, and terpenoids at a concentration of 0.5% to 40% by mass; heating the composition to provide at least 1 milligram of cannabidiol vapor; and inhaling the cannabidiol vapor, in which: the composition is a liquid; the composition has a viscosity of less than 50 pascal-seconds at a temperature of either 70 degrees Fahrenheit or 21 degrees Celsius; the one or more solutes are dissolved in the cannabidiol; the composition comprises molecules having a boiling point lower than either 360 degrees Fahrenheit or 182 degrees Celsius at a combined concentration of at least 95% by mass; the composition lacks propylene glycol, glycerol, triglycerides, phospholipids, fatty acids, and waxes at a combined concentration greater than 5% by mass; the composition has either a freezing point or a gas-liquid transition temperature of less than either 70 degrees Fahrenheit or 21 degrees Celsius; the container is configured to position the composition in thermal communication with a heating element; heating the composition comprises conductively heating at least a portion of the composition to a temperature of at least 330 degrees Fahrenheit or 165 degrees Celsius; and conductively heating at least a portion of the composition comprises transferring heat from the heating element to the portion of the composition.

In some embodiments, a method to administer cannabidiol comprises providing a container containing a composition comprising cannabidiol at a concentration of 60% to 99.5% by mass and one or more solutes selected from one or more of alpha-bisabolol, beta-caryophyllene, guaiol, humulene, limonene, myrcene, and terpinolene at a combined concentration of 0.5% to 40% by mass; heating the composition to provide at least 1 milligram of cannabidiol vapor; and inhaling the cannabidiol vapor, in which: the composition is a liquid; the composition has a viscosity of less than 50 pascal-seconds at a temperature of either 70 degrees Fahrenheit or 21 degrees Celsius; the one or more solutes are dissolved in the cannabidiol; the composition comprises molecules having a boiling point lower than either 360 degrees Fahrenheit or 182 degrees Celsius at a combined concentration of at least 95% by mass; the composition lacks propylene glycol, glycerol, triglycerides, phospholipids, fatty acids, and waxes at a combined concentration greater than 5% by mass; the composition has either a freezing point or a gas-liquid transition temperature of less than either 70 degrees Fahrenheit or 21 degrees Celsius; the container is configured to position the composition in thermal communication with a heating element; heating the composition comprises conductively heating at least a portion of the composition to a temperature of at least 330 degrees Fahrenheit or 165 degrees Celsius; and conductively heating at least a portion of the composition comprises transferring heat from the heating element to the portion of the composition.

The following examples provide a framework to implement certain aspects of the disclosure, and these examples do not limit the scope of this patent document or any claim that matures from the disclosure of this patent document.

EXEMPLIFICATION

Example 1. Production of Compositions Comprising Cannabidiol that do not Crystallize Cannabinoids were extracted from organic industrial hemp using the system described in PCT Patent Application Publication No. 2016/161420 A1 to produce crude industrial hemp extract comprising 65-70% cannabidiol; 5-10% terpenes, terpene alcohols, and terpenoids; 2-3% tetrahydrocannabinol; and other volatile molecules including waxes and phospholipids. The crude industrial hemp extract formed crystals of cannabidiol when stored at room temperature for 24 hours.

The cannabinoids of the crude industrial hemp extract were separated from other molecules by distillation in a VTA Short Path Distillation Plant VKL 70 (Verfahrenstechnische Anlagen GmbH & Co. KG, Germany) to produce a cannabinoid distillate comprising approximately 90% cannabidiol and 5% tetrahydrocannabinol. 10 grams of the cannabinoid distillate was combined with 0.1 grams of a terpene, terpene alcohol, and terpenoid blend obtained from True Terpenes (Oregon, USA) with heating to produce a liquid composition. The blend contained beta-caryophyllene (41%), humulene (18%), linalool (13%), limonene, alpha-bisabolol, nerolidol, beta-pinene, citronellol, fenchol, and other molecules at lower concentrations.

The liquid composition was stored at room temperature for 1 year with intermittent exposure to light and air, and the composition produced no detectable crystals. Cooling the liquid below room temperature vitrified the composition into a glass without any detectable crystal formation.

This example demonstrates that small amounts of terpenes, terpene alcohols, and terpenoids can provide robust stabilization of cannabidiol in a liquid state and inhibit crystal formation over commercially-relevant timeframes, even when subjected to chemical stress, provided that lipids that comprise fatty acids are removed from the liquid state.

What is claimed is:

1. A composition, comprising cannabidiol at a concentration of 50% to 99.5% by mass and one or more solutes selected from terpenes, terpene alcohols, and terpenoids at a combined concentration of 0.5% to 40% by mass, in which:
the one or more solutes are dissolved in the cannabidiol;
the composition has either a freezing point or a glass-liquid transition temperature; and
the freezing point or the glass-liquid transition temperature is either at least 50 degrees Fahrenheit less than the freezing point of pure cannabidiol or at least 27 degrees Celsius less than the freezing point of pure cannabidiol.

2. The composition of claim 1, in which:
the composition has a freezing point;
the composition lacks a glass-liquid transition temperature; and
the freezing point is less than either 70 degrees Fahrenheit or 21 degrees Celsius.

3. The composition of claim 1, in which:
the composition has a glass-liquid transition temperature;
the composition lacks a freezing point; and
the glass-liquid transition temperature is less than either 70 degrees Fahrenheit or 21 degrees Celsius.

4. The composition of claim 1, in which the composition lacks crystals of cannabidiol.

5. The composition of claim 1, in which the composition comprises cannabidiol at a concentration of 75% to 99% by mass.

6. The composition of claim 1, in which the composition lacks tetrahydrocannabinol at a concentration greater than 0.3% by mass.

7. The composition of claim 1, in which:
the composition comprises tetrahydrocannabinol at a concentration greater than 0.3% by mass;
the tetrahydrocannabinol is dissolved in the cannabidiol; and
the composition comprises cannabidiol and tetrahydrocannabinol at a ratio of 3:1 to 200:1 by mass.

8. The composition of claim 1, comprising (6aS,10aR)-6,6,9-trimethyl-3-pentyl-6a,7,8,10a-tetrahydro-6H-benzo[c]chromen-1-ol at a concentration of 0.05% to 5% by mass, in which the (6aS,10aR)-6,6,9-trimethyl-3-pentyl-6a,7,8,10a-tetrahydro-6H-benzo[c]chromen-1-ol is dissolved in the cannabidiol.

9. The composition of claim 1, in which the composition comprises molecules having a boiling point lower than either 360 degrees Fahrenheit or 182 degrees Celsius at a combined concentration of at least 95% by mass.

10. The composition of claim 1, in which the composition lacks propylene glycol, glycerol, triglycerides, phospholipids, fatty acids, and waxes at a combined concentration greater than 5% by mass.

11. The composition of claim 1, in which the composition is a liquid.

12. The composition of claim 11, in which the composition has a viscosity, and the viscosity is less than 100 pascal-seconds at a temperature of either 70 degrees Fahrenheit or 21 degrees Celsius.

13. The composition of claim 12, in which the viscosity is 50 millipascal-seconds to 50 pascal-seconds at a temperature of either 70 degrees Fahrenheit or 21 degrees Celsius.

14. The composition of claim 1, in which the one or more solutes comprise one or more of alpha-bisabolol, alpha-phellandrene, alpha-pinene, alpha-terpinene, alpha-terpineol, beta-caryophyllene, beta-pinene, borneol, cadinene, camphene, camphor, caryophyllene oxide, citral, citronellol, delta-3-carene, eucalyptol, eugenol, gamma-terpinene, geraniol, guaiol, humulene, isopulegol, limonene, linalool, myrcene, nerol, nerolidol, ocimene, para-cymene, phytol, pulegone, terpineol, terpinolene, and valencene at a combined concentration of 0.5% to 40% by mass.

15. The composition of claim 1, in which the one or more solutes comprise one or more of alpha-bisabolol, beta-caryophyllene, guaiol, humulene, limonene, myrcene, and terpinolene at a combined concentration of 0.5% to 40% by mass.

16. The composition of claim 1, in which:
the composition comprises cannabidiol at a concentration of 65% to 99% by mass;
the composition lacks crystals of cannabidiol;
the composition lacks tetrahydrocannabinol at a concentration greater than 0.3% by mass;
the one or more solutes comprise one or more of alpha-bisabolol, beta-caryophyllene, guaiol, humulene, limonene, myrcene, and terpinolene at a combined concentration of 0.5% to 35% by mass;
the composition comprises molecules having a boiling point lower than either 360 degrees Fahrenheit or 182 degrees Celsius at a combined concentration of at least 95% by mass;
the composition lacks propylene glycol, glycerol, triglycerides, phospholipids, fatty acids, and waxes at a combined concentration greater than 5% by mass;
the composition has a glass-liquid transition temperature;
the glass-liquid transition temperature is less than either 70 degrees Fahrenheit or 21 degrees Celsius;
the composition lacks a freezing point;
the composition is a liquid; and
the composition has a viscosity, and the viscosity is 50 millipascal-seconds to 50 pascal-seconds at a temperature of either 70 degrees Fahrenheit or 21 degrees Celsius.

17. The composition of claim 1, in which:
the composition comprises cannabidiol at a concentration of 65% to 99% by mass;
the composition lacks crystals of cannabidiol;
the composition comprises tetrahydrocannabinol at a concentration greater than 0.3% by mass;
the tetrahydrocannabinol is dissolved in the cannabidiol;
the composition comprises cannabidiol and tetrahydrocannabinol at a ratio of 3:1 to 200:1 by mass;
the one or more solutes comprise one or more of alpha-bisabolol, beta-caryophyllene, guaiol, humulene, limonene, myrcene, and terpinolene at a combined concentration of 0.5% to 35% by mass;
the composition comprises molecules having a boiling point lower than either 360 degrees Fahrenheit or 182 degrees Celsius at a combined concentration of at least 95% by mass;

the composition lacks propylene glycol, glycerol, triglycerides, phospholipids, fatty acids, and waxes at a combined concentration greater than 5% by mass;

the composition has a glass-liquid transition temperature;

the glass-liquid transition temperature is less than either 70 degrees Fahrenheit or 21 degrees Celsius;

the composition lacks a freezing point;

the composition is a liquid; and the composition has a viscosity, and the viscosity is 50 millipascal-seconds to 50 pascal-seconds at a temperature of either 70 degrees Fahrenheit or 21 degrees Celsius.

* * * * *